United States Patent [19]

Czech et al.

[11] Patent Number: 5,187,103
[45] Date of Patent: Feb. 16, 1993

[54] COLORIMETRIC METHOD AND REAGENT FOR THE ASSAY OF LITHIUM IN A TEST SAMPLE

[75] Inventors: Bronislaw P. Czech, Peekskill; Eddy Chapoteau, Brooklyn; Anand Kumar, Monroe, all of N.Y.

[73] Assignee: Miles Inc., Tarrytown, N.Y.

[21] Appl. No.: 648,073

[22] Filed: Jan. 31, 1991

[51] Int. Cl.⁵ .................. G01N 33/20; G01N 21/78
[52] U.S. Cl. ........................... 436/79; 436/74; 436/171; 436/501; 540/467; 540/469
[58] Field of Search .............. 436/74, 79, 164, 169, 436/73, 170, 805, 171, 172, 178, 501; 422/55, 56, 57; 540/467, 469, 468

[56] References Cited

U.S. PATENT DOCUMENTS 4,808,539  2/1989  Chapoteau et al. ............ 436/79
4,994,395  2/1991  Chapateau et al. ............ 436/74
5,045,475  9/1991  Chapoteau et al. ............ 436/74

Primary Examiner—James C. Housel
Assistant Examiner—David Redding
Attorney, Agent, or Firm—Jeffrey M. Greenman

[57] ABSTRACT

A chromogenic cryptand found to be especially selective in the determination of lithium in blood of the general formula (I):

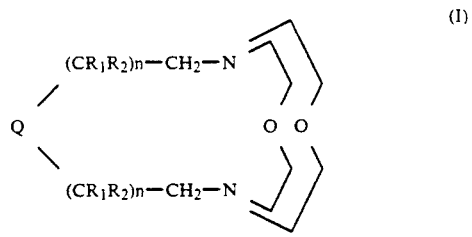

where:
n = 1 or 2,
$R_1$ and $R_2$, same or different, are hydrogen, lower alkyl, lower alkenyl, or lower alkylidene; and
Q is a chromogenic moiety capable of providing a detectable response upon complexation of said compound with lithium ion and has the structure:

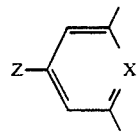

wherein:
X is CH, C—OH or N; and Z is p-nitrophenylazo, 2,4-dinitrophenylazo, 2,4,6-trinitrophenylazo, p-nitrostyryl, p-benzoquinonemonoimino, bis-(4-dimethylaminophenyl) hydroxymethyl, 3-phenylisothiazolyl-5-azo, thiazolyl-5-azo; or isothiazolyl-5-azo.

A reagent composition and synthesis of a preferred chromogenic cryptand are also disclosed.

10 Claims, 9 Drawing Sheets

COLORIMETRIC METHOD AND REAGENT FOR THE ASSAY OF LITHIUM IN A TEST SAMPLE

BACKGROUND OF THE INVENTION

1. Field of the Invention

The present invention relates to a novel method and reagent useful for the measurement of lithium ions, in particular, lithium ions in blood and other physiological fluids.

2. Description of the Prior Art

The determination of lithium ion concentration has application in monitoring medical therapy. Specifically, lithium carbonate is frequently used in the treatment of manic depression and other psychiatric disorders, and the measurement of the lithium level in blood aids the physician in monitoring lithium drug therapy. Needless to say, a rapid, easy-to-perform method for determining the presence and concentration of a lithium ion in aqueous samples would greatly enhance such treatment.

Current methods for lithium measurement in clinical samples use flame photometry and only very recently ion-selective electrodes (ISE). An accurate determination of lithium in clinical samples by the ISE method is difficult and cumbersome, mainly due to interferences from sodium and other ions present in serum. To eliminate this problem a concurrent sodium measurement is required.

Lithium selective chromoionophores have been described in several publications. The first lithium specific chromogenic corand was described by G. E. Pacey et al., Synth. Commun. 11, 1981, 323-328. A chromogenic "crowned" phenol selective for lithium was described by T. Kaneda et al., Tetrahedron Lett. 22, 1981, 4407-4408. A chloroform solution of this compound gave a 160 nm bathochromic shift to a purple-red color upon contact with excess solid LiCl or LiClO$_4$ (but not other salts) in the presence of pyridine. S. Ogawa et al., J. Am. Chem. Soc. 106, 1984, 5760-5762, reported a chromogenic compound which upon contact with LiCl in a methylene chloride solution turned from red to colorless. K. Sasaki et al., Anal. Chim. Acta 174, 1985, 141-149, reported another chromogenic corand which was used for the determination of lithium in an extraction system. Misumi et al., J. Am. Chem. Soc. 107, 1985, 4802-4803, synthesized a chromogenic spherand which acted as a lithium specific indicator for solid lithium salts of soft anions but was too weak a binder to strip water from Li(H$_2$O)$_6$+. A cation extraction study with a series of lithium-selective chromogenic corands was published by K. Kimura et al., J. Org. Chem. 52, 1987, 836-844. A. S. Attiyat et al., Microchem. J. 37, 1988, 114-121, described the spectrophotometric measurement of lithium in the presence of sodium using TMC-crown formazane. Another chromogenic spherand reported by D. J. Cram et al., J. Am. Chem. Soc. 110, 1988, 571-577 was capable of detecting lithium and sodium in an 80% dioxane-20% water system. Many of these prior art procedures require extraction-photometric procedures that are difficult to automate; sample pre-treatment and poor selectivity make them unattractive as alternatives to ISE or flame photometry. The relatively low therapeutic level of lithium in serum (0.5-1.5 mM) imposes very high constraints on selectivity over the high normal serum sodium concentration (135-150 mM). Ideally, the selectivity for lithium over sodium should be 1,500:1 in order to essentially eliminate any sodium interference.

The compounds of the present invention can generally be described as chromogenic (1.1.0) cryptands. Certain cryptands are known to have high selectivity for complexing with cations, and if coupled with chromophores, yield intensive color reactions that can be evaluated analytically. For example, Vogtle U.S. Pat. No. 4,367,072 describes a process for determining ions employing chromogenic cryptands. It is essentially based on ion-selective complexation between the ion to be determined and a complexing agent and measurement of the extinction change occurring during complexing. The complexing agent is bonded with a chromophore.

Klink, et al. European Patent Publication 85,320 discloses a potassium reagent and a procedure for determining potassium ions. The reagent contains a compound of general formula

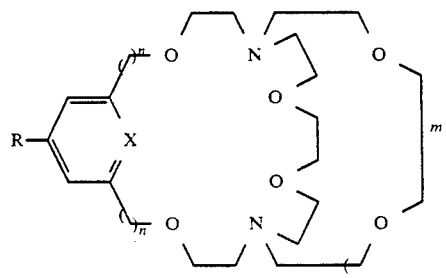

where n and m=0 or 1, X=N or COH and R=p-nitrophenylazo, 3-phenylisothiazolyl-5-azo, isothiazolyl-5-axo, thiazolyl-5-azo, 2,4,6-trinitrophenylazo, p-nitrostyryl, p-benzoquinonemonoimino and bis- (p-dimethylaminophenyl) hydroxy-methyl. The potassium ions are determined in a reaction medium consisting of water and at least one water-miscible organic solvent and in the presence of an organic base.

Both the Vogtle and Klink, et al. structures have larger size cavities designed for complexation with potassium ions. An ionophore for lithium, on the other hand, must have a much smaller and more pre-organized cavity in order to complex with the small=: lithium ion.

The fundamental difficulty in the design of lithium selective chromoionophores lies in the fact that lithium is the third smallest element (after hydrogen and helium) with ionic diameter of 1.20 (Na+1.90Å; K+2.66Å). The task then involves design and synthesis of an ionophore with a small cavity which is inflexible so as to exclude other ions from interaction for high selectivity and which possesses the binding sites preorganized complementarily for lithium complexation to achieve high sensitivity. The small cavity size puts severe strain on the cyclic structure making the synthesis of such ionophore extremely difficult. In general, the monocyclic crown ethers with small cavities, which are relatively easier to synthesize, have failed to meet the selectivity and sensitivity requirements because of lack of preorganization of the binding sites.

The major difference between the cryptands of the present invention and structures of the cryptands reported earlier by Vogtle, et al. and Klink, et al. is the lack of oxygen atoms in the side arms linking the cyclic diamine moiety with the aromatic subunit. It is known to those skilled in the art that such structural modifications usually lead to the loss of binding power by the cryptand and are not expected to be beneficial. However, quite unexpectedly, we discovered that the cryptands of this invention, devoid of side-arm oxygen arms, are able to bind lithium exclusively and fully discriminate over sodium. The removal of these oxygens from the side arms enabled us to construct cryptands with cavities in which the lithium ion can be held tightly and very fittingly. In addition, examination of molecular models indicates that the loss of oxygen binding sites is well compensated by the gain in preorganization of the cryptand cavity.

Accordingly, it has been found that the chromogenic cryptands of the present invention demonstrate particular sensitivity to lithium ions. The chromogenic cryptand can be incorporated into a reagent adapted for use on automated clinical analyzers to determine the lithium concentration in physiological fluid samples such as blood.

OBJECTS OF THE INVENTION

It is an object of this invention to provide a novel assay method and reagent composition useful for the measurement of lithium ions, in particular, lithium ions in blood and other physiological fluids.

Another object of this invention is to provide an assay method and reagent composition as above, which enable fast assay of the ion.

Yet another object of this invention is to provide an assay method and reagent composition as above which have a high degree of selectivity.

Still another object of this invention is to provide an assay method and reagent composition as above which are particularly adapted for photometric clinical analyzers.

A yet further object of this invention is to provide an assay method and reagent composition as above which provide an accurate, precise and convenient alternative to conventional flame photometry and ISE methodologies.

A yet further object of this invention is to provide a dry test device in which the reagent composition, as above, is incorporated into a matrix.

A further object of this invention is to provide an assay method and reagent composition as above which permit the quantitative determination of lithium in blood serum and other biological fluids by spectrophotometric methods in a homogeneous, single phase solvent system that requires no sample pretreatment.

Other objects and features of the invention will be in part apparent and in part pointed out hereinafter.

SUMMARY OF THE INVENTION

Briefly stated, the present invention resides in the discovery of a new chromogenic cryptand (1.1.0) of the formula (I):

(I)

where:
n = 1 or 2,
$R_1$ and $R_2$, same or different, are hydrogen, lower alkyl, lower alkenyl, or lower alkylidene; and
Q is a chromogenic moiety capable of providing a detectable response upon complexation of the compound with lithium ion and has the structure:

wherein:
X is CH, C-OH or N; and
Z is p-nitrophenylazo, 2,4-dinitrophenylazo, 2,4,6-trinitrophenylazo, p-nitrostyryl, p-benzoquinonemonoimino, bis-(4-dimethylaminophenyl) hydroxymethyl, 3-phenylisothiazolyl-5-azo, thiazolyl-5-azo; or isothiazolyl-5-azo.

A chromogenic cryptand of the present invention which has been found to be especially selective in the determination of lithium in blood is p-nitrophenylazophenol (1.1.0) cryptand of formula (II):

(II)

where in formula (I):
n = 1;
$R_1 = R_2 = H$;
X = COH; and
Z is p-nitrophenylazo.

The compound of formula (I) may be incorporated into a reagent for detecting the presence of lithium in solution. The reagent composition comprises a compound of general formula (I), a percentage (by volume to volume) of a water miscible organic solvent and a buffer. A preferred reagent composition includes the p-nitrophenylphenol (1.1.0) cryptand of formula (II), a volume percentage of water to organic solvent of about 10% and a buffer present in an amount to adjust the pH of the reagent composition to at least about 12. Optionally, a surfactant may be added to the reagent composition to heighten sensitivity to lithium.

A further part of the present invention is a process of synthesizing the preferred chromogenic cryptand of the present invention.

The scope of the invention, including the compound, reagent composition and their use, synthesis and preparation, and experimental results are set forth hereinbelow.

BRIEF DESCRIPTION OF THE DRAWINGS

The above and other objects and significant advantages of the present invention are believed made clear by the following detailed description thereof taken in conjunction with the accompanying drawings wherein.

DESCRIPTION OF THE PREFERRED EMBODIMENTS

Figure 1:
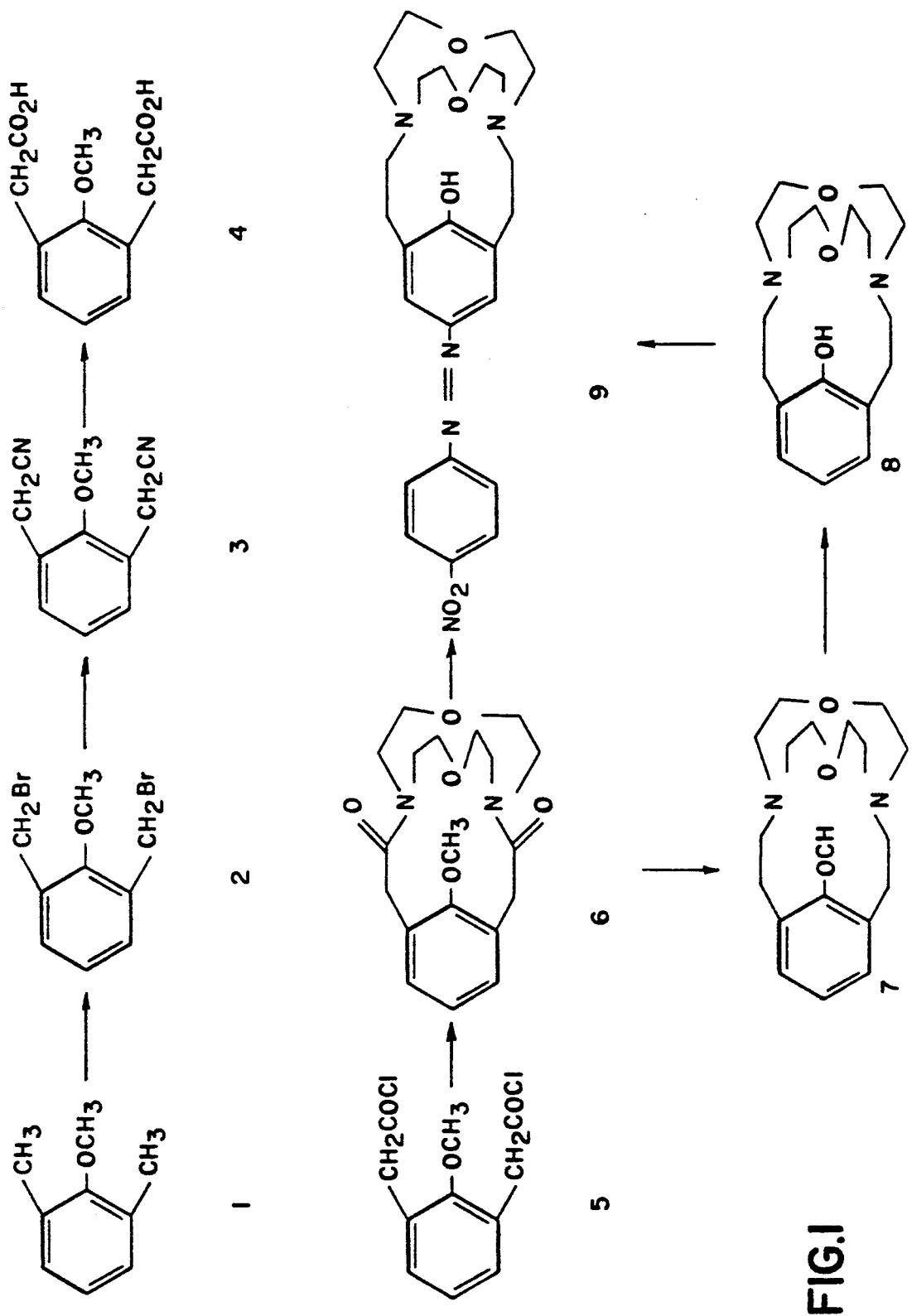
FIG. 1 describes a reaction pathway for synthesizing p-nitrophenylazophenol (1.1.0) cryptand.

The following definitions are provided to clarify the scope of the present invention, and to enable its formulation and use.

As used herein, "chromogenic" is intended as meaning that characteristic of a chemical system whereby a detectable response is generated in response to an external stimulus. Thus, for example, an ionophore is chromogenic where it is capable of exhibiting a detectable response upon complexing with an ion, which detectable response is not limited solely to change in color as defined below.

By the term "detectable response" is meant a change in or appearance of a property in a system which is capable of being perceived, either by direct observation or instrumentally, and which is a function of the presence of a specific ion in an aqueous test sample. Some examples of detectable responses are the change in or appearance of color, fluorescence, phosphorescence, reflectance, chemiluminescence, or infrared spectrum which are referred to generally as chromogenic responses. Other examples of detectable responses may be the change in electrochemical properties, pH and nuclear magnetic resonance.

The term "lower alkyl", as used in the present disclosure, includes an alkyl moiety, substituted or unsubstituted, containing about 1–4 carbon atoms. Included in the meaning of lower alkyl are methyl, ethyl, n-propyl, isopropyl, n-butyl, sec-butyl, and tertbutyl. These may be unsubstituted, or they may be substituted provided any such substituents do not interfere with the operation or functioning of the presently claimed test means or device in its capability to detect lithium ions. "Lower alkylidene" is used in the same context as "lower alkyl", but designates an alkylene or alkylidene group (i.e. a divalent alkyl) having 1–4 carbon atoms. Thus, lower alkylidene includes methylene, ethylidene, n-propylidene, isopropylidene, n-butylidene, sec-butylidene and tert-butylidene. "Lower alkenyl" means vinyl or lower alkyl substituted vinyl.

Compound (I) includes as part of its structure a particular kind of chemically configured moiety, Q, which is capable of changing its physico-chemical characteristics when a complex is formed by the lithium ion and compound of general formula (I). That is to say, if the lithium ion is present in a test sample whether or not other ions are present, a detectable change in those physico-chemical properties takes place. This capability to exhibit such a response to complexation contributes greatly to the usefulness of compound (I) in assaying the analyte, or target, ion.

In general, the chromogenic moiety Q has the structure

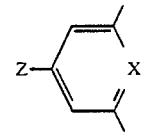

wherein:
X is CH, C-OH or N; and
Z is p-nitrophenylazo, 2,4-dinitrophenylazo, 2,4,6-trinitrophenylazo, p-nitrostyryl, p-benzoquinonemonoimino, bis-(4-dimethylaminophenyl) hydroxymethyl, 3-phenylisothiazolyl-5-azo, thiazolyl-5-azo, or isothiazolyl-5-azo.

The compounds of formula (I) or (II) previously described can be incorporated in a reagent composition which, when prepared as an aqueous solution, was found useful for detecting the presence of lithium ions. A preferred reagent composition includes, in addition to a compound of formula (II), a water miscible organic solvent at a concentration of ten (10) percent volume to volume. Suitable organic solvents are cyclic ethers such as dioxan, tetrahydrofuran; ethylene glycol and derivatives such as mono-methylethylene glycol, mono-ethyl glycol, mono-propyl glycol, mono-butyl glycol; amides such as formamide, dimethylformamide, pyrrolidine, N-alkyl pyrrolidine (methyl); aliphatic alcohols such as methanol, ethanol, isopropanol, n-propanol, butanols; sulfoxides such as dimethylsulfoxide; amino alcohols such as ethanolamine, propanolamine, amino propanediols; and ketones such as acetone, methylethylketone. The reagent composition also includes a buffer to provide a pH environment of at least 12. Optionally, a surfactant may be included. In addition, the reagent composition may contain manufacturing excipients, stabilizers and other inert ingredients, all of which are easily within the knowledge of one skilled in the art, or which could be routinely determined without the need for undue experimentation.

The reagent composition may be in liquid form when used, or may be impregnated into a suitable carrier matrix to form a test device. The device can take on such formats as a dip-and-read strip for urine or a test slide for use with an automatic blood analyzer, or can form a multi-layer structure such as is described in U.S. Pat. Nos. 3,992,158 and 4,292,272.

EXPERIMENTAL

The following examples set forth various aspects of the subject invention. It will be understood that the formulations and procedures which follow are provided for the purposes of illustration only and that other ingredients, proportions and procedures can be employed in accordance with the disclosures of this invention.

Materials and Methods

Unless specified otherwise, reagent grade reactants and solvents were used as received from chemical suppliers. Diaza-12-crown-4 was prepared according to the procedure disclosed in U.S. Pat. No. 4,900,818. Benzene was dried over molecular sieves. Radical-free tetrahydrofuran was distilled from sodium benzophenone ketyl prior to use.

Melting points were determined on a Thomas-Hoover capillary apparatus. IR spectra were obtained with a Perkin-Elmer 267 spectrophotometer. $^1$H and $^{13}$C NMR spectra were measured with a Varian Gemini 200 MHz spectrometer and chemical shifts are reported in parts per million ($\delta$) downfield from tetramethylsilane. Elemental analysis was performed by SPANG Microanalytical Laboratory of Eagle Harbor, Mich.

1 Synthesis of p-nitrophenylazophenol (1.1.0) Cryptand

The synthesis sequence is illustrated in FIG. 1.

Preparation of 2,6-di(bromomethyl)anisole (2)

2,6-dimethylanisole (1), 36.0 g, 0.26 mol), N,N'-dibromo-5,5-dimethyl-hydantoin (85.8 g, 0.30 mol), and benzyl peroxide (1.20 g) were combined in a one liter flask containing 300 ml of carbon tetrachloride. Irradiation was conducted by placing a 500 watt tungsten lamp two inches from the reaction flask for two hours. The reaction mixture was cooled to room temperature and washed with water. The organic layer was dried over anhydrous magnesium sulfate and the solvent was removed in vacuo. The orange oil was treated with methanol and a white crystalline solid (52.16 g, 72%) was collected, m.p. 83.5°–85.5° C. $^1$H NMR (CDCl$_3$): 4.02 (s, 3H), 7.06–7.17 (m, 1H), 7.37 (d, 2H); $^{13}$C NMR (CDCl$_3$) 27.5, 62.2, 125.0, 131.9, 132.2, 156.0.

Preparation of 2,6-di(cyanomethyl)anisole (3)

A solution of 2,6-di(bromomethyl)anisole (2), 10.00 g, 34.0 mmol) in benzene (40 ml) was added to a flask containing sodium cyanide (8.33 g, 0.17 mol) and hexadecyldimethylethylammonium bromide (1.00 g, 2.66 mmol) in 20 ml of water. The heterogeneous solution was rapidly mixed with a mechanical stirrer at reflux for five hours. To the reaction mixture was added 100 ml each of benzene and water. After separation, the aqueous layer was extracted with an additional 50 ml of benzene. The organic layers were combined and dried over anhydrous sodium sulfate. Evaporation in vacuo gave a yellow oil which was column chromatographed on alumina with dichloromethane as the eluent to give 6.00 g (95%) of dinitrile (3) as a white solid, m.p. 58°–59.5° C. IR (melt) 2252 (CN) cm$^{-1}$; $^1$H NMR (CDCl$_3$) 3.78 (s, 4H), 3.84 (s, 3H), 7.20 (t, 1H), 7.43 (d, 2H); $^{13}$C NMR (CDCl$_3$): 18.4, 61.4, 117.5, 124.4, 125.4, 130.0. Anal. Calcd for C$_{11}$H$_{10}$N$_2$O: C, 70.95; H, 5.41. Found: C, 71.01; H, 5.39.

Preparation of 2,6-di(carboxymethyl)anisole (4)

Dinitrile (3) (11.00 g, 59.0 mmol) in 300 ml of 7% sodium hydroxide solution was refluxed overnight. After cooling to room temperature, the solution was extracted with methylene chloride (2×80 ml) to remove any unreacted starting material. The pH of the aqueous layer was adjusted to 2 by careful addition of 5% sulfuric acid. The mixture was allowed to stand for one hour and a white precipitate was filtered. To the resulting white solid, 200 ml of tetrahydrofuran was added and the mixture was filtered to remove sodium sulfate. Evaporation of the solvent gave a white solid which was washed with ether to produce 11.9 g (91%) of dicarboxylic acid (4), m.p. 184°–186° C. IR (deposit): 3500–2750 (COOH), 1698 (C=O) cm$^{-1}$; $^1$H NMR (DMSO-d$_6$) 3.57 (s, 4H), 3.69 (s, 3H), 6.95–7.10 (m, 1H), 7.13 (d, 2H); $^{13}$C NMR (DMSO-d$_6$): 35.4, 60.9, 123.9, 128.6, 130.5, 156.7, 173.0. Anal. Calcd for C$_{11}$H$_{12}$O$_5$: C, 58.93; H 5.39. Found: C, 59.11; H, 5.51.

Preparation of Diacid Chloride (5)

Oxalyl chloride (1.13 g, 9.80 mmol) and two drops of dry pyridine were added to a suspension of diacid (4) (0.50 g, 2.20 mmol) in 25 ml of anhydrous benzene. After stirring for two days at room temperature, the mixture was filtered and the solvent was evaporated in vacuo to give 0.59 g (98% yield) of the diacid chloride (5) as a light yellow oil. IR (neat): 1801 (C=O) cm$^{-1}$; $^1$H NMR (CDCl$_3$) 3.64 (s, 3H), 4.09 (s,4H) 7.00–7.20 (m, 3H); $^{13}$C NMR (CDCl$_3$): 47.5, 61.5, 124.9, 131.7, 156.8, 171.7.

Preparation of Cryptand Diamide (6)

A solution (400 ml) of diacid chloride (5) (2.71 g, 10.38 mmol) in dry benzene and a solution (400 ml) of diaza-12-crown-4 (1.81 g, 10.38 mmol) and triethylamine (2.58 g, 25.50 mmol) in benzene were added simultaneously at room temperature with two syringe pumps at the addition rate of 20 ml/H to 415 ml of vigorously stirred benzene. After the addition was completed, the stirring was continued for six hours. The solvent was removed in vacuo and the residue was column chromatographed on flash silica gel using methylene chloride-methanol (95:5) as eluent to afford 2.10 g (57%) of diamide (6) as a white solid, m.p. 278°–280° C. IR (deposit): 1630 (C=O), 1142 (C—O) cm$^{-1}$; $^1$H NMR (CDCl$_3$) 2.58–2.76 (m, 4H), 3.05–3.26 (m, 4H), 3.40–3.95 (m, 15H), 7.00 (s, 3H); $^{13}$C NMR (CDCl$_3$): 41.6, 45.9, 49.7, 59.3, 68.1, 69.2, 124.7, 130.2, 131.2, 160.6, 172.1. Anal. Calcd for C$_{19}$H$_{26}$N$_2$O$_5$: C, 62.97; H, 7.23. Found: C, 63.05; H, 7.26.

Preparation of Cryptand (7)

A solution of diamide (6) (1.00 g, 2.76 mmol) in dry methylene chloride (55 ml) was added dropwise to a cooled (ice bath) suspension of lithium aluminum hydride (0.42 g, 11.07 mmol) in dry tetrahydrofuran (95 ml). The mixture was stirred at room temperature and followed by TLC. After 22 hours, the substrate disappeared and the reaction was quenched by addition of ethyl acetate. The inorganic material was filtered, washed extensively with methylene chloride, and the residue obtained after evaporation of the solvent was chromatographed on a short alumina (basic, deactivated) column using methylene chloride-methanol (0–15%) to give a yellow solid which was extracted several times with ethyl ether. The solvent was then evaporated to produce cryptand (7) (0.44 g, 47%) as white crystals which decompose above 130° C. $^1$H NMR (CDCl$_3$) 1.98–2.58 (m, 12H), 2.88–3.34 (m, 10H), 3.51 (s, 3H), 3.55 (t, 1H), 3.60 (t, 1H); $^{13}$C NMR (CDCl$_3$) 27.49, 54.29, 55.42, 61.25, 62.29, 69.70, 72.03, 123.41, 127.21, 134.81, 161.61. MS 334 (M+). Anal. Calcd for C$_{19}$H$_{30}$N$_2$O$_3$: C, 68.23; H, 9.04. Found: C, 68.11; H, 9.18.

Preparation of Cryptand-Phenol (8)

A mixture of crytand (7) (0.44 g, 1.31 mmol), sodium thioethoxide (0.28 g, 3.38 mmol) and lithium bromide (0.22 g, 2.51 mmol) in dry dimethylformamide (9 ml) was heated at 150°–155° C. over 5 hours. The solvent was removed in vacuo and the residue was redissolved in methylene chloride and filtered. The solvent was evaporated and the crude product was purified by column chromatography on alumina using methylene chloride-methanol (1%) to give cryptand-phenol (8) (0.25 g, 60%) as a white crystalline solid with mp 116.5°–117.5° C. $^1$H NMR (CDCl$_3$) 1.85–2.6 (M, 12H), 2.85–3.8 (m, 12H), 6.8–7.0 (m, 3H), 7.58 (S, 1H), $^{13}$C NMR (CDCl$_3$) 28.71, 53.08, 55.47, 61.58, 69.69, 72.00, 122.12, 126.97, 135.32, 155.74; MS 320 (M+). Anal. Calcd for C$_{18}$H$_{28}$N$_2$O$_3$: C, 67.47; H, 8.81. Found: C, 67.30; H, 8.92.

Preparation of Chromogenic Compound (9)

Two alternative methods, A and B, can be used.

Method A

Cryptand diamide (6), (0.95 g, 2.62 mmol) was added portionwise to a suspension of lithium aluminum hydride (0.82 g, 21.61 mmol) in dry tetrahydrofuran (80 ml) and the mixture was refluxed for over 15 hours. After cooling, 2.5 ml of 5% aqueous lithium hydroxide was added carefully. The inorganic material was filtered and washed extensively with tetrahydrofuran. Evaporation of the solvent gave a red viscous oil which was dissolved in 5 ml of tetrahydrofuran and five drops of 32% aqueous sodium hydroxide were added. The solvent was removed in vacuo and 4 ml of glacial acetic acid was added to the residue. To this solution, p-nitrobenzenediazonium chloride (made at 0°–5° C. from p-nitroaniline (0.35 g), 1 N HCl (7.8 ml) and sodium nitrite (0.21 g)) was added dropwise with stirring. During the addition, the pH was monitored and adjusted to neutral with 5% sodium hydroxide. The reaction mixture turned from colorless to red-brown and was stirred overnight at room temperature. The solvent was removed in vacuo and the residue was partitioned between methylene chloride and water. The organic layer was washed several times with dionized water, the solvent was evaporated and the residue was column chromatographed twice on deactivated basic alumina using chloroform and chloroform-ethanol (95:5) as eluent to afford 0.12 g (10% yield from two steps) of chromogenic cryptand (9) as a red crystalline solid which decomposes over 210° C. $^1$H NMR (CDCl$_3$) 1.5–3.5 (m, 24H), 7.68 (s, 2H), 8.17 (ABq, 4H); $^{13}$C NMR (CDCl$_3$) 28.96, 54.23, 61.30, 70.71, 123.16, 123.49, 125.18, 136.65, 148.40, 148.64, 156.87, 161.05; MS 469 (M+). Anal. Calcd for C$_{24}$H$_{31}$N$_5$O$_5$: C 61.39; H, 6.65. Found: C, 61.18; H, 6.82.

Method B

Cryptand-phenol (8) (380 mg, 1.19 mmol) was dissolved in THF (5 ml) and 32% aqueous NaOH (3 drops) was added. The mixture was sonicated, the solvent was removed in vacuo and the residue was redissolved in glacial acetic acid (2 ml). p-Nitrobenzenediazonium chloride (generated from p-nitroaniline (172 mg, 1.245 mmol), 1N HCl (3.7 ml) and NaNO$_2$ (97 mg, 1.41 mmol)) was added dropwise. The red colored solution was stirred overnight at room temperature. The usual workup and purification (as above) gave 400 mg (72%) of the pure product.

2 Analytical Studies

Materials and Methods 1M tetramethylammonium hydroxide (TMAOH) was purchased from Southwestern Analytical Chemicals. Diethylene glycol monoethyl ether (DEGMEE) was obtained from Kodak. Triton X-100, Brij-35 and butylated hydroxyanisole (BHA) were received from ICI and Sigma Chemicals, respectively. Analytical grade NaCl, KCl, and LiCl were used to determine the response of p-nitrophenylazophenol (1.1.0) cryptand to cations. Cyclohexylaminopropane sulfonic acid (CAPS) was obtained from Calbiochem. All materials were used as received. The correlation samples were both a gift from Lincoln Hospital, a Mental Rehabilitation Center in Bronx, N.Y. and purchased by the Technicon Evaluation Laboratory.

A. Spectral Properties of p-nitrophenylazophenol (1.1.0) Cryptand

The UV-VIS spectra of p-nitrophenylazophenol (1.1.0) cryptand in complexation with various ions, i.e. Na+K+, and Li+, were determined in 1 to $2\times10^{-4}$M solutions of the cryptand in 2 to 50% volume to volume (v/v) DEGMEE in water. A $1\times10^{-2}$M stock solution of the cryptand was prepared in DEGMEE. Typically, the solutions were prepared as follows: for the spectral characteristics in 10% v/v DEGMEE, 0.2 ml of the stock solution was added to 0.8 ml DEGMEE. The diluted cryptand was quantitatively transferred to 9.0 ml of the appropriate reagent and mixed. 1N HCl was used to obtain the acid form (HL) and 1M TMAOH for the base form of the cryptand which is designated in the following tables as L. Tne resulting solutions were scanned from 700 to 300 nm on a Beckman DU-8 spectrophotometer. The spectra of the cation complexes of p-nitrophenylazophenol (1.1.0) cryptand in 10% v/v DEGMEE/1M TMAOH were obtained by adding 0.02 ml LiCl, KCl, NaCl, all 1N to their respective cuvettes containing 2 ml of reagent and scanned from 700 to 300 nm.

B. Evaluation of the Reagent

The lithium reagent composition was evaluated on a TECHNICON RA-1000® analyzer marketed by Technicon Instruments Corporation. (TECHNICON RA-1000® is a registered trademark of Technicon Instruments Corporation, Tarrytown, N.Y.) For the correlation study and the determination of the concentration of lithium in the standards and calibrators, the IL flame photometer served as the reference. For the interference study, the potentially interfering substances were weighed into human pooled sera purchased from Biocell.

Results and Discussion

Spectral Properties

Table I records the wavelength maxima and absorptivities of p-nitrophenylazophenol (1.1.0) cryptand when exposed to Na+, K+ and Li+ ions in 10% v/v DEGMEE.

TABLE I

|      | λmax (nm) |     | ε (M⁻¹ cm⁻¹) |       |
|------|-----------|-----|--------------|-------|
|      | 1         | 2   | 1            | 2     |
| HL   | 494       | 363 | 8,800        | 8,000 |
| L    | 575       | 378 | 8,000        | 8,000 |
| L Na⁻ | 575      | 374 | 7,980        | 8,050 |
| L K⁻ | 572.5     | 374 | 7,900        | 8,060 |
| L Li⁻ | 517      | 375 | 7,000        | 7,950 |

The spectrum of the acid form of p-nitrophenylazophenol (1.1.0) cryptand shows two wavelength maxima (Table I) of equivalent absorptivities, which indicates the presence of two distinct forms of the chromophore. The p-nitrophenylazophenol (1.1.0) cryptand exhibits two peaks only when there is strong hydrogen bonding between the phenolic hydrogen and the cavity. Higher than usual pKa of p-nitrophenylazophenol (1.1.0) cryptand in 10% DEGMEE-water, as determined spectrophotometrically, confirms this phenomenon. Larger cavity analogs to the cryptand were synthesized, in which hydrogen bonding is reduced, and these showed lower pKa values of the chromophore (Table II).

TABLE II

|     | p-nitrophenylazophenol (1.1.0) cryptand | extended (1.1.0) cryptand | (2.2.0) cryptand |
|-----|------------------------------------------|---------------------------|------------------|
| pKa | 12.6                                     | 11.5                      | 11.1             |

The structures of the extended (1.1.0) cryptand and cryptand (2.2.0) analogs are shown below. Extended (1.1.0) is the cryptand of formula (I) wherein n = 2.

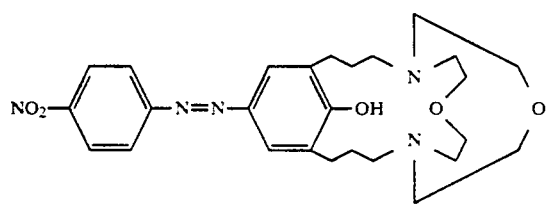

Extended (1.1.0)

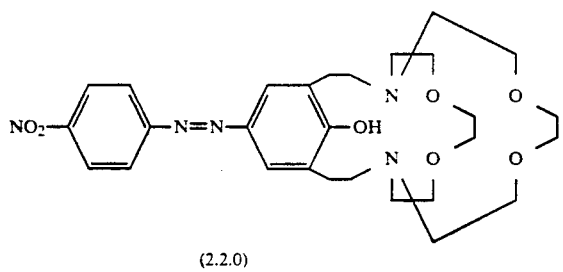

(2.2.0)

The increase in the cavity size in the analogs resulted in the loss of selectivity and sensitivity. The extended cryptand (1.1.0) gave very good response to lithium in the extraction mode. The (2.2.0) cryptand is more selective for potassium over sodium and lithium.

Figure 2:
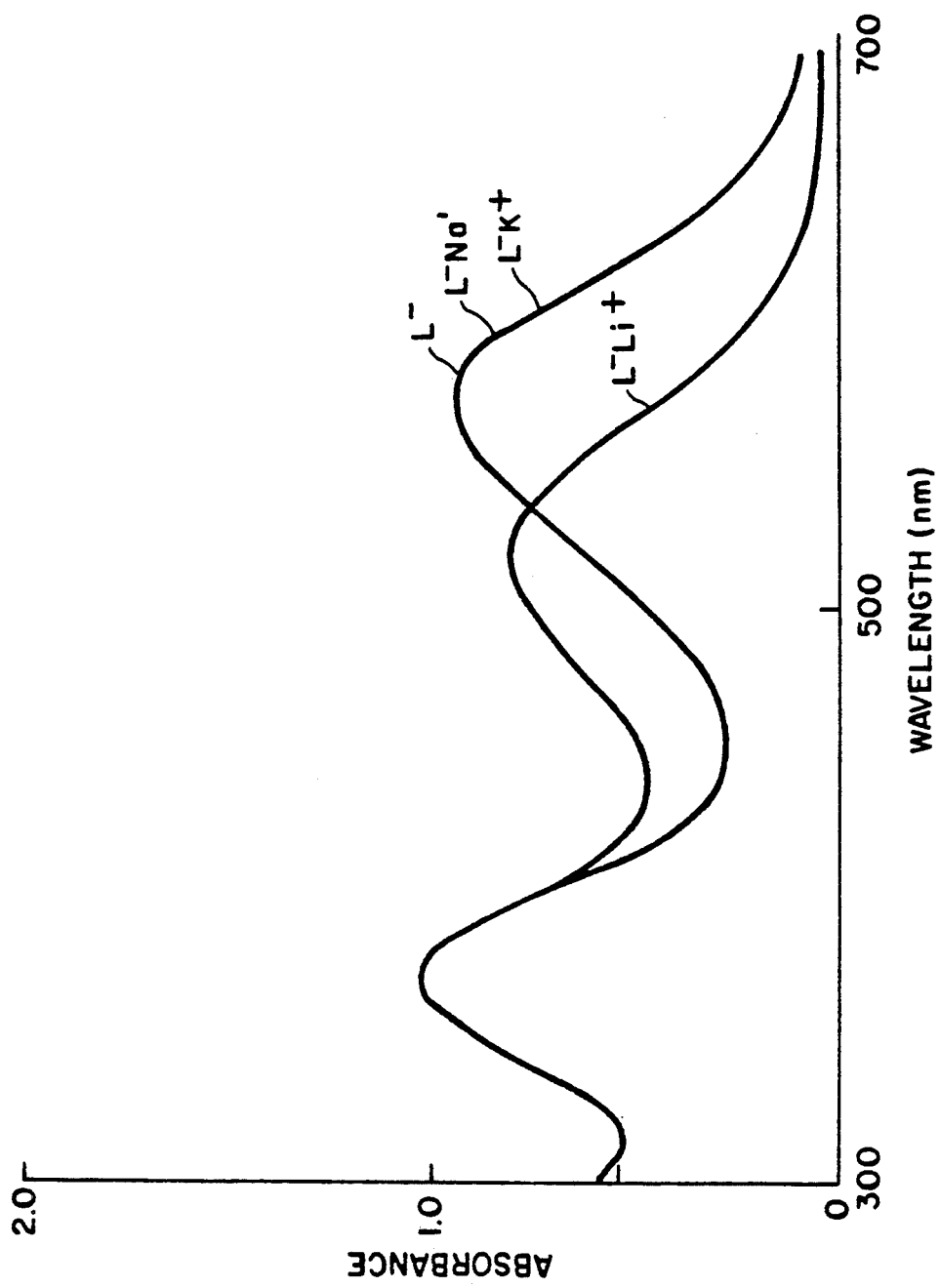
FIG. 2 illustrates the photometric response of p-nitrophenylazophenol (1.1.0) cryptand to cations.

The ionized base form did not exhibit either a spectral shift or a change in absorptivity in the presence of excess Na⁺ complex (L Na⁺) or K⁺ complex (L K⁺). A substantial hypsochromic shift (58 nm) was obtained with Li complex (L Li⁺) as shown in FIG. 2.

The response to cations at pH 11.0 to 12.5 was also determined in a similar manner. A zwitterionic buffer CAPS was used (Table III).

TABLE III

Effect of pH on response to cations in 10% v/v DEGMEE.

|       | λ max (ε)     |              |     |              |
|-------|---------------|--------------|-----|--------------|
|       | 12.0          |              | 11.0 |             |
| pH    | 1             | 2            | 1   | 2            |
| L     | —             | 379 (13,300) | —   | 380 (13,800) |
| L Na⁺ | —             | 379 (13,300) | —   | 380 (13,800) |
| L K⁺  | —             | 379 (13,300) | —   | 380 (13,800) |
| L Li⁺ | 512 (8,800)   | 379 (12,600) | —   | 380 (13,800) |

L = base form of p-nitrophenylazophenol (1.1.0) cryptand

Figure 3:
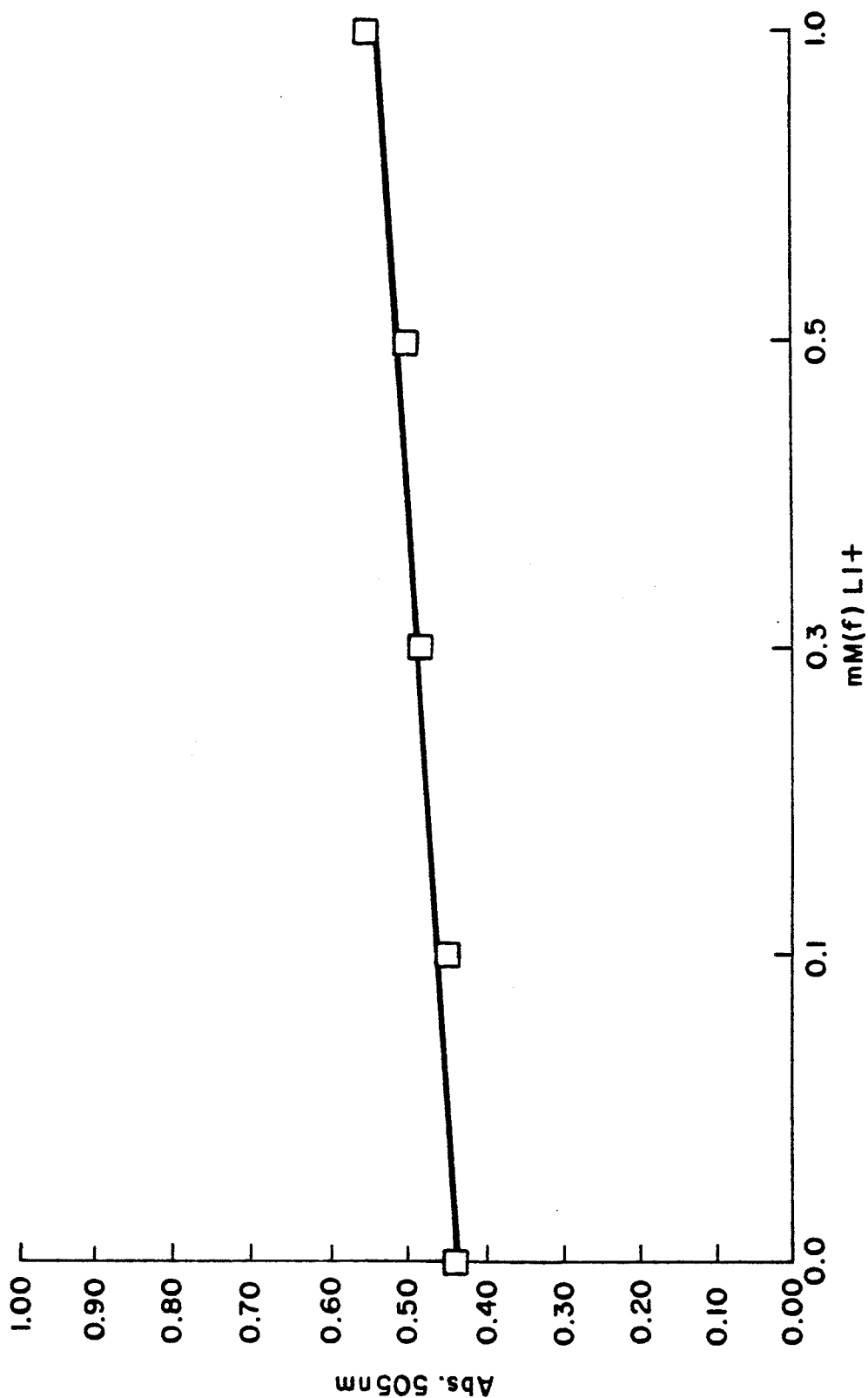
FIG. 3 illustrates the sensitivity of p-nitrophenylazophenol (1.1.0) cryptand to lithium.

A bathochromic shift with concurrent increase in absorptivity is obtained between pH 12.0 and 13.0 as shown in FIG. 3.

A high degree of ionization of the chromoionophore is necessary to obtain good sensitivity. Unlike other ionizable chromoionophores where color formation is obtained through the loss of a proton, induced by complexation of a cation, p-nitrophenylazophenol (1.1.0) cryptand exhibits a different mechanism of response. The cooperative relationship between complexation and electrostatic interaction of the lithium cation with the ionized phenolic moiety of the cryptand is believed responsible for the colorimetric response to lithium.

Effect of Organic Solvent

In general, macrocyclic ionophores require low dielectric, non-polar solvents for strong complexation with the cations. This is because in polar solvents such as water, the hydration of the cation as well as the binding sites of the ionophore weakens the complexation by several orders of magnitude. Thus the goal for a chromoionophore configuration is to build in a high degree of complexation with the target cation so that good sensitivity could be realized in an essentially aqueous medium despite the loss in binding ability due to hydration. A small proportion of a watermiscible organic solvent in the reagent provides desired sensitivity without any deletrious effect on the system.

Figure 4:
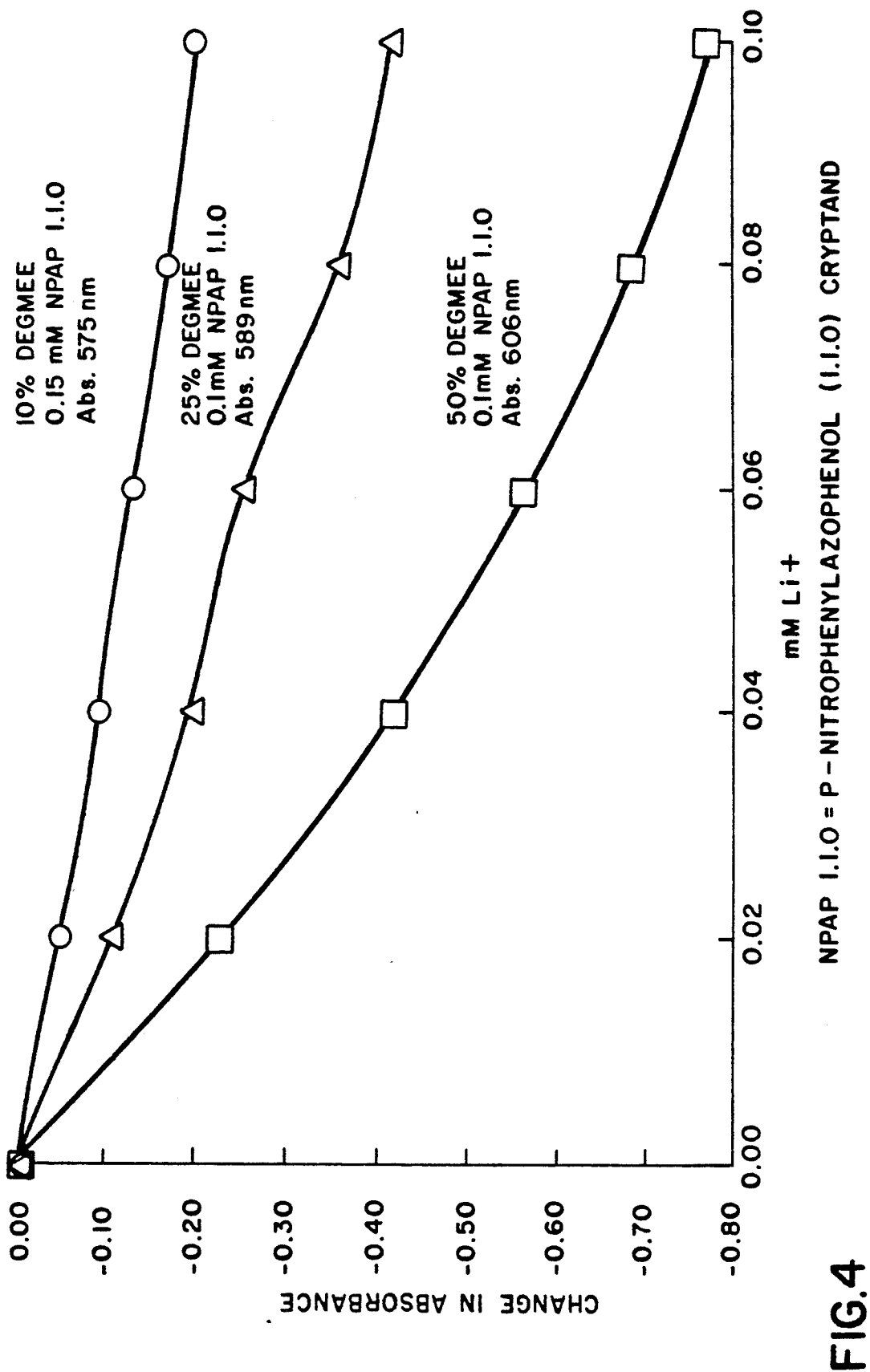
FIG. 4 illustrates the effect of organic solvent concentration on the sensitivity of p-nitrophenylazophenol (1.1.0) cryptand.

As expected, high concentration of solvent increases the sensitivity of p-nitrophenylazophenol (1.1.0) cryptand to lithium as shown in FIG. 4.

However, high concentration of solvent also affects the selectivity; at 25% DEGMEE, interference by 140 mM Na⁺ corresponds to 0.1 mM Li⁺, which is not acceptable for clinical purposes. The selectivity requirements of the lithium assay are high, in certain cases where the concentration of lithium is near 0.1 mM, the molar ratio of Li⁺:Na⁺ is about 1:1500. 10% DEGMEE appeared to be the optimum condition for selectivity and sensitivity. Lower DEGMEE concentration can be used with some loss of sensitivity. At 2.5% DEGMEE, the response to lithium is reduced by 25%.

Effect of Surfactant

Non-ionic surfactants are known to interact with monoazo dyes producing a disturbance of the electronic spectrum. Both, Brij-35 and Triton X-100 at 1% w/v caused a substantial bathochromic shift of the λmax and an increase in the absorptivities of both p-nitrophenylazophenol (1.1.0) cryptand and its lithium complex as shown in Table IV.

TABLE IV

Effect of non-ionic surfactant on wavelength maxima and absorptivities of p-nitrophenylazophenol (1.1.0) cryptand.

| | $\lambda_{max}(\epsilon)$ | | | |
|---|---|---|---|---|
| | L | LNa⁻ | LK⁻ | LLi⁻ |
| 0.0 | 572 | 574 | 572 | 517 |
| | (7,300) | (7,300) | (7,300) | (6,300) |
| 1.0% BRIJ-35 | 602 | 601 | 601 | 534 |
| | (17,600) | (17,510) | (17,500) | (16,240) |
| 1.0% Triton X-100 | 604 | 604 | 604 | 534 |
| | (12,100) | (12,000) | (12,000) | (14,800) |

L = base form of p-nitrophenylazophenol (1.1.0) cryptand

Figure 5:
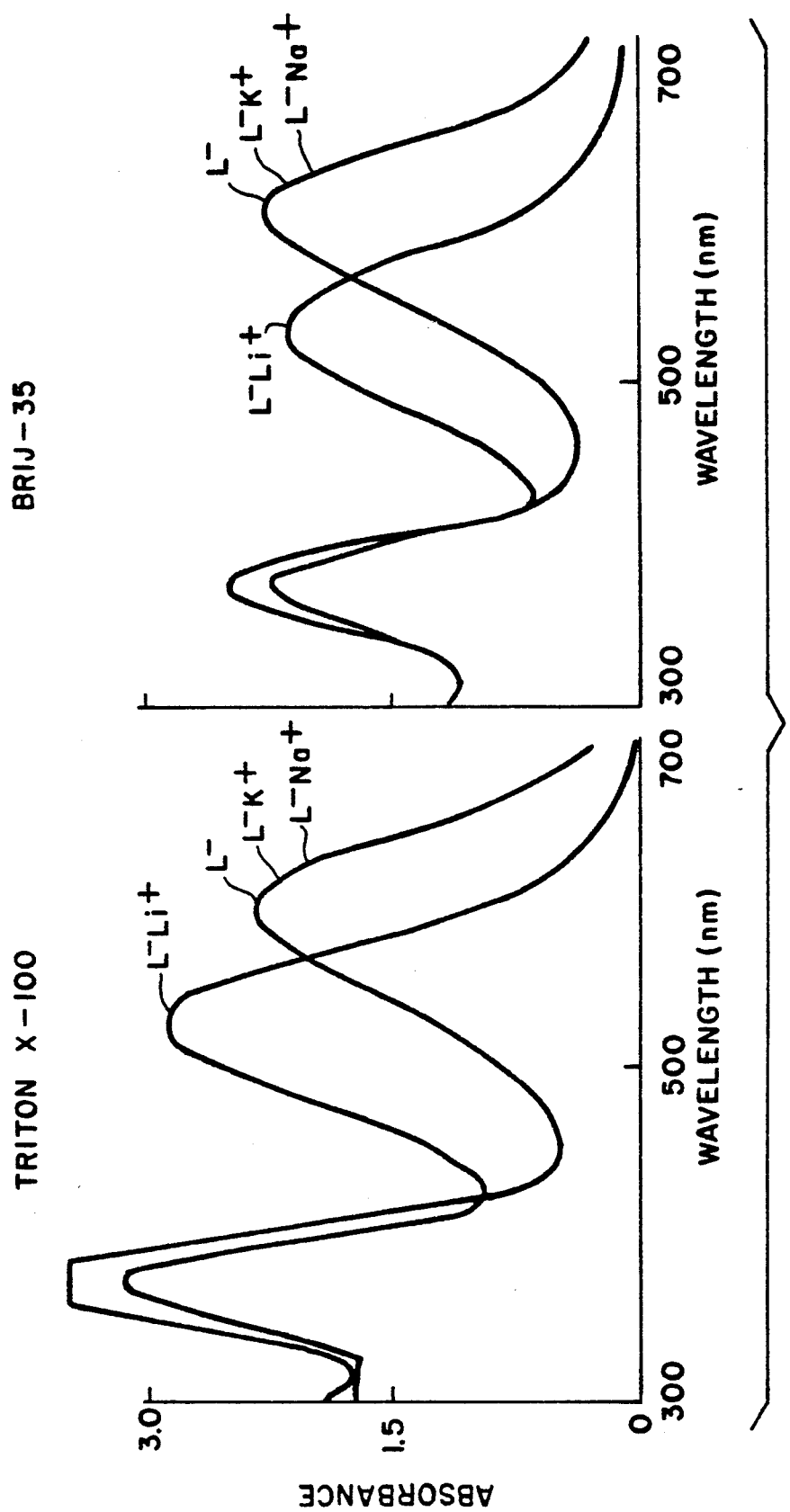
FIG. 5 illustrates the electronic spectrum of p-nitrophenylazophenol (1.1.0) cryptand in the presence of surfactants.

The added cations ($K^+$, $Na^+$) produced no change in the spectra indicating that the surfactant had no effect on the selectivity of the cryptand as illustrated in FIG. 5.

Thus, the incorporation of a surfactant in the reagent provided increased sensitivity and the added benefit of decreasing the interaction of serum proteins with the cryptand.

Analytical Wavelength

Figure 6:
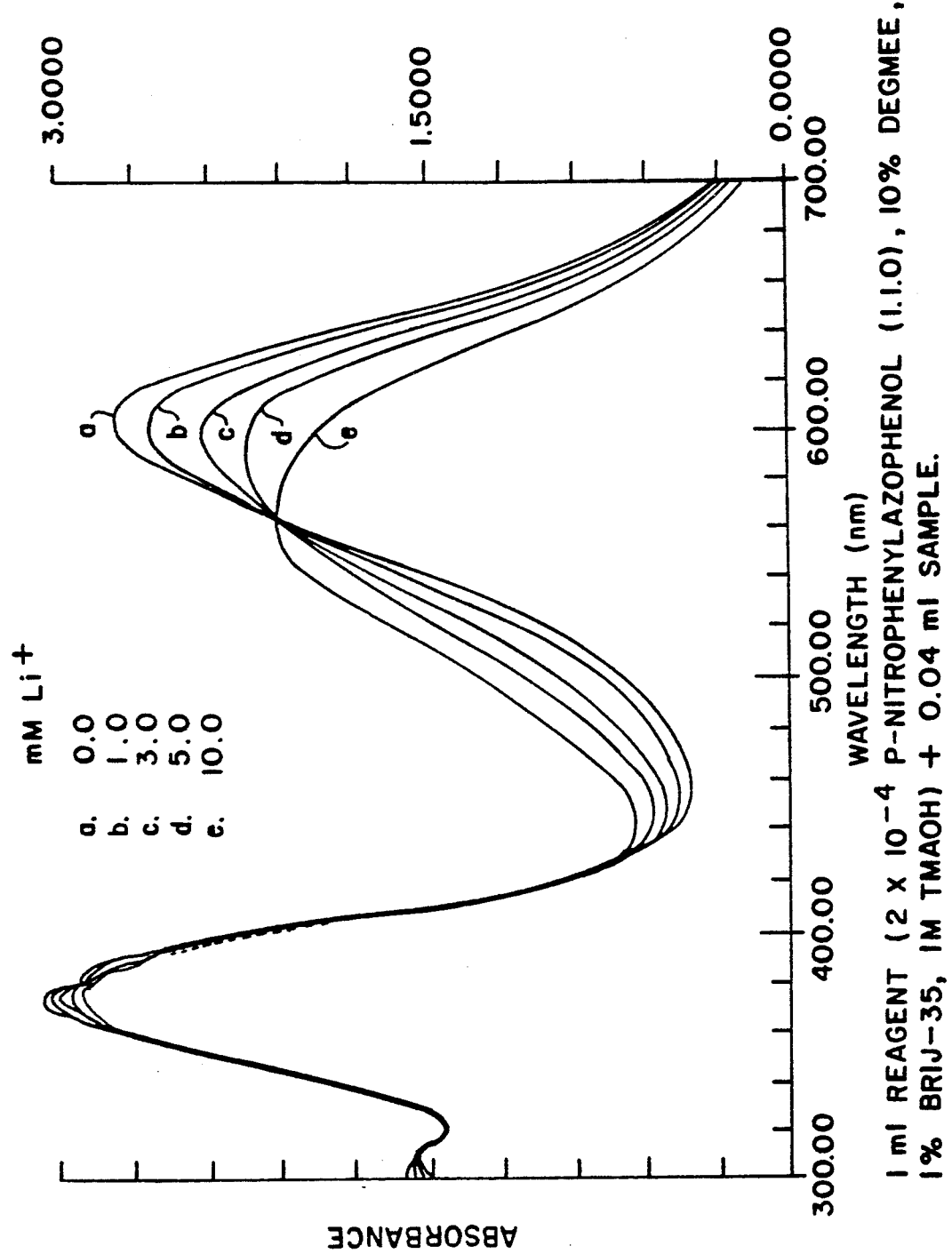
FIG. 6 is the spectral response of p-nitrophenylazophenol (1.1.0) cryptand to lithium.

The spectral response of the p-nitrophenylazophenol (1.1.0) cryptand to lithium is shown in FIG. 6. The data suggests that the response can be measured as either a decrease in absorbance at 600 nm or an increase of the lithium complex at 534 nm.

Selectivity

Figure 7:
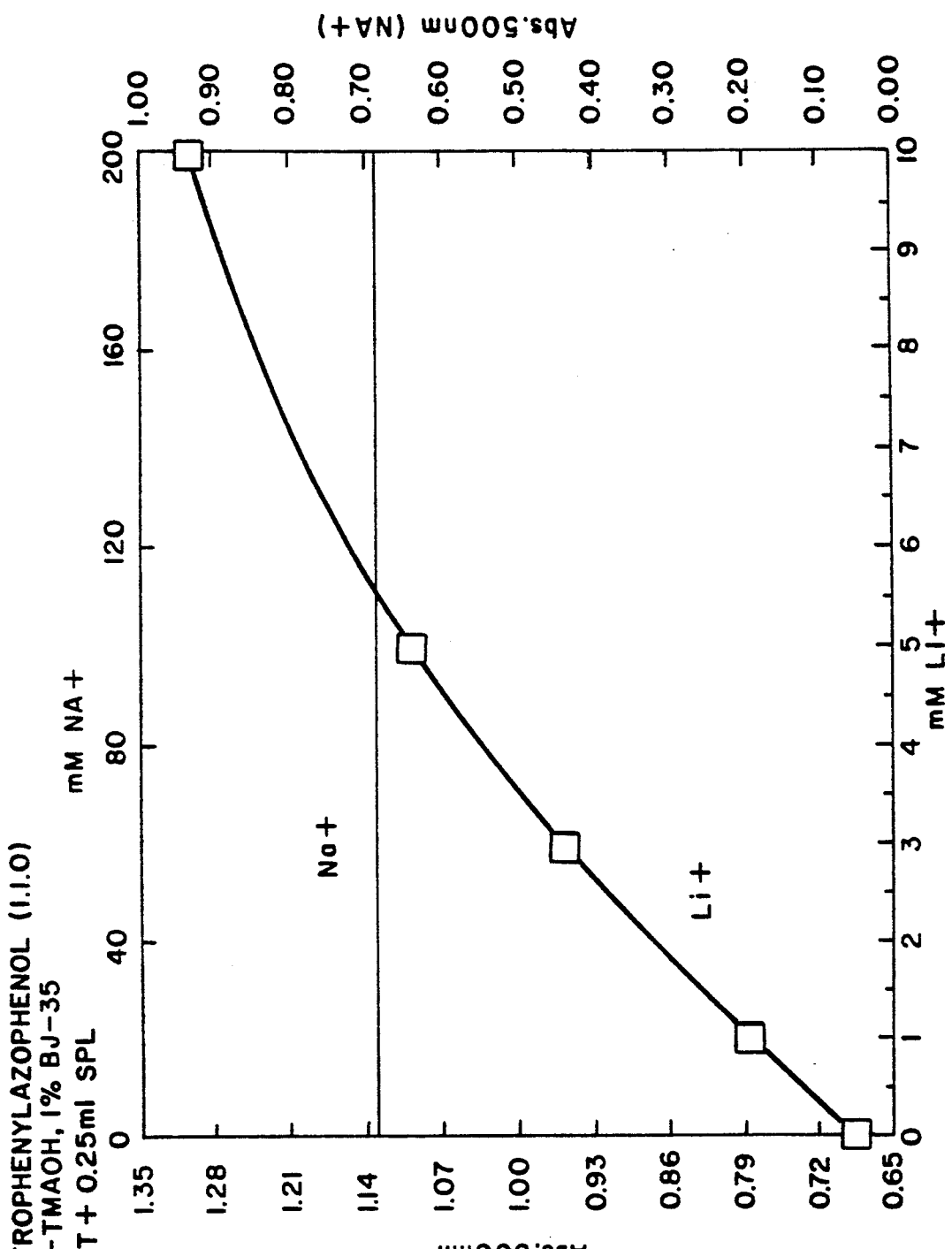
FIG. 7 is a plot of the selectivity data for p-nitrophenylazophenol (1.1.0) cryptand.

Sample to reagent ratio of 1:40 gave good sensitivity and almost total selectivity over sodium as shown in FIG. 7. By taking the ratio of the slope of the respective response curves, one obtains approximate selectivity of 4000:1 for $Li^+/Na^+$. Other potential interfering cations such as $K^+$, $Ca^{2+}$, $Mg^{2+}$ and $Fe^{3+}$, present in human serum do not induce spectral response in the chromoionophore. The cavity effectively inhibits their interaction with the ionized phenolic group.

Evaluation on a TECHNICON RA-1000® Analyzer

The following formulation of the chromogenic reagent was evaluated on the TECHNICON RA-1000® analyzer:

$2.0 \times 10^{-4}$M p-nitrophenylazophenol (1.1.0) cryptand
10% DEGMEE (v/v)
1.0% BRIJ-35 (w/v)
0.01% BHA (w/v)
1M TMAOH The instrument parameters were:

| Reagent volume | 390 ul |
|---|---|
| Sample volume | 10 ul |
| Delay | 2 min. |
| Filter | 500 nm |
| Type | Endpoint |

A. Linearity

Figure 8:
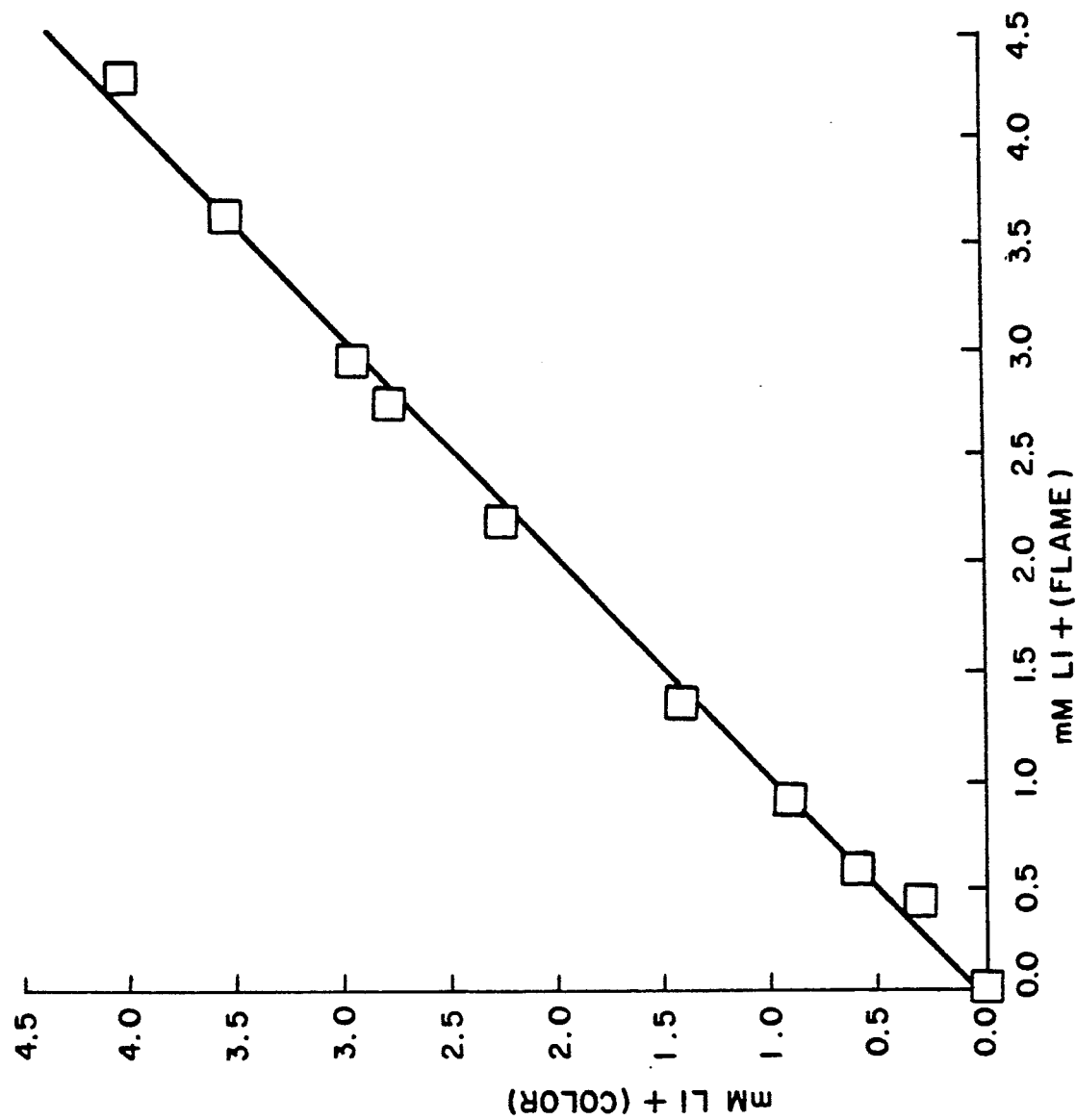
FIG. 8 is a plot of the linearity data for the reagent incorporating p-nitrophenylazophenol (1.1.0) cryptand.

Linearity pools were prepared by adding known amounts of lithium chloride to human pool serum. The lithium concentrations of the linearity samples were assigned with a flame photometer. By using the 1.0 mM LiCl linearity sample as the calibrator, the linearity was found to be 0.0-3.5 mM Li with a maximum deviation of -3% at 3.5 mM as shown in FIG. 8.

B. Interference

Table IV shows the results of an interference study. Most of the potential interfering substances present in human serum did not show any interference. Salicylate and ascorbate also do not cause interference even at very high concentrations. Icteric samples with bilirubin up to 10 mg/dl did not require sample blank correction. Samples with higher bilirubin levels as well as lipemic samples could require blank correction.

TABLE IV

| | recovered mM $Li^+$ |
|---|---|
| Pool serum⁺ | 1.00 |
| 2 mM NH₄Cl | 1.00 |
| 85 mg/dl Lactic Acid | 1.00 |
| 150 mg/dl Ethanol | 1.00 |
| 4 g/dl HSA | 0.98 |
| 50 mg/dl Salicylate | 0.98 |
| 4 g/dl Glucose | 0.99 |
| 50 mg/dl Ascorbic Acid | 0.98 |
| 50 mg/dl Creatinine | 0.98 |
| 50 mg/dl Urea | 1.02 |
| 50 mg/dl Uric Acid | 1.00 |
| 200 mM NaCl | 0.98 |
| 500 mM NaCl | 0.98 |
| 2.4 mM $Fe^{+3}$ | 1.03 |
| 5 mM $Mg^{+2}$ | 1.00 |
| 5 mM $Ca^{+2}$ | 1.00 |
| 10 mM $K^+$ | 0.98 |
| 60 mg/dl Hb (1% hemolysis) | 1.13 |
| 10 mg/dl Bilirubin | 1.00 |

The interfering substances were added to pool serum containing 1.0 mM LiCl.

C. Correlation

Figure 9:
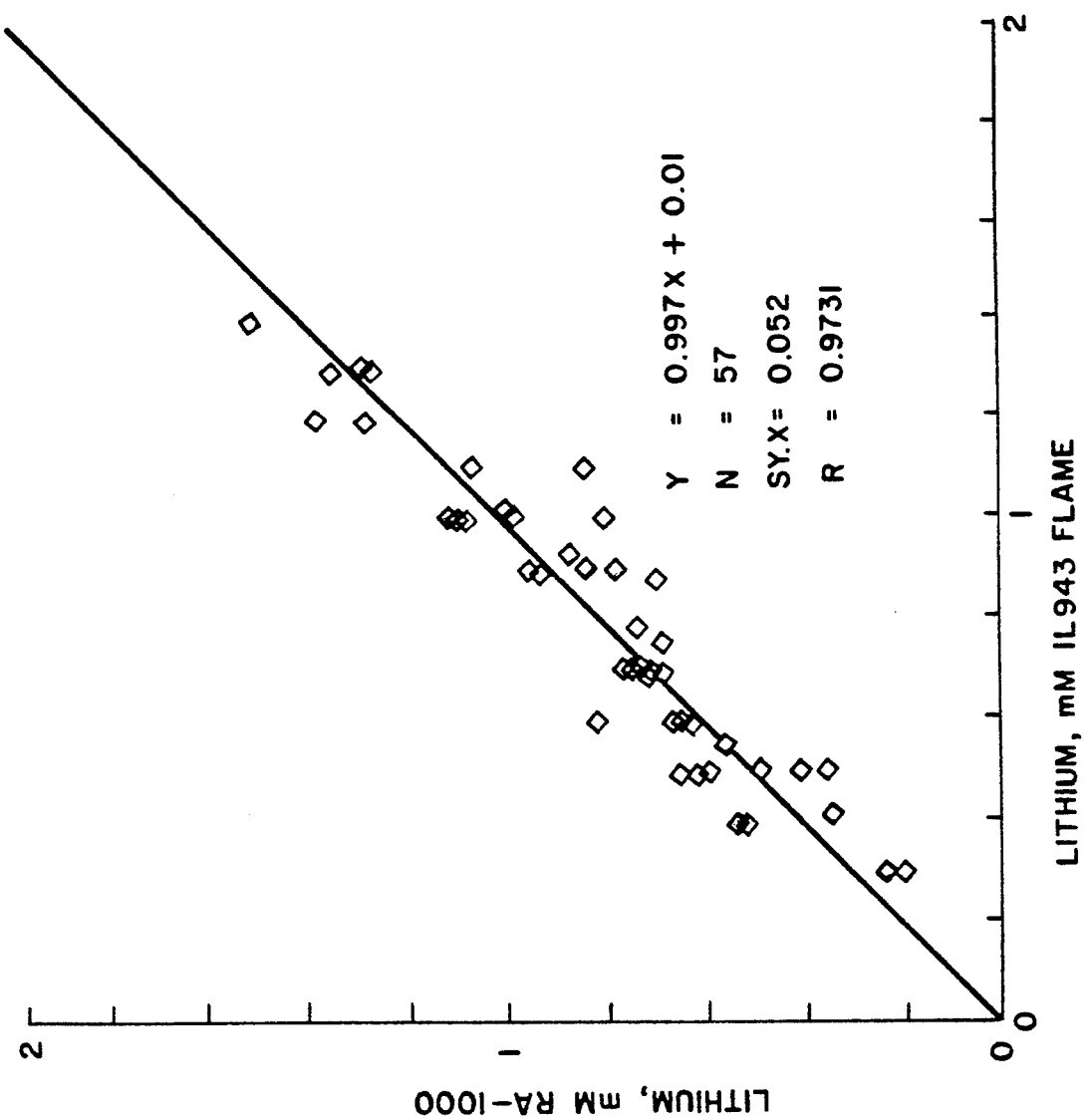
FIG. 9 is the correlation data for the reagent composition including p-nitrophenylazophenol (1.1.0) cryptand as compared to the standard IL flame photometric method.

The correlation of the method vs. the IL flame photometer was very good as shown in FIG. 9. All the samples used were real patient sera. NIST reference material SRM 909 was used as the control for the correlation.

Some advantages of the present invention evident from the foregoing description include an assay method and reagent composition utilizing p-nitrophenylazophenol (1.1.0) cryptand which permits the quantitative determination of lithium in blood serum and other biological fluids by spectrophotometric methods in a homogeneous, single phase solvent system that requires no sample pretreatment. The resultant assay method and reagent composition can be easily adapted for use on an automated clinical blood analyzer.

As various changes can be made in the above compositions and method without departing from the scope of the invention, it is intended that all matter contained in the above description, or shown on the accompanying drawings, shall be interpreted as illustrative, not in a limiting sense.

What is claimed is:

1. A chromogenic cryptand having the structure:

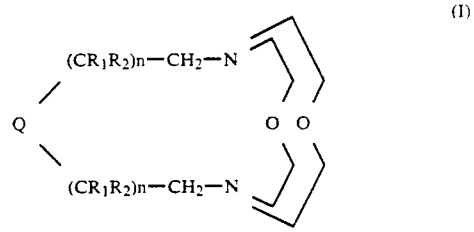

(I)

where:

n = 1 or 2,

R₁ and R₂, same or different, are hydrogen, lower alkyl, lower alkenyl, or lower alkylidene; and Q is a chromogenic moiety which provides a detectable response upon complexation of said compound with lithium ion and has the structure:

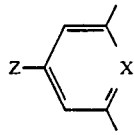

wherein:

X is CH, C-OH or N; and Z is p-nitrophenylazo, 2,4-dinitrophenylazo, 2,4,6-trinitrophenylazo, p-nitrostyryl, p-benzoquinonemonoimino, bis-(4-dimethylaminophenyl) hydroxymethyl, 3-phenylisothiazolyl-5-azo, thiazolyl-5-azo, or isothiazolyl-5-azo.

2. The chromogenic cryptand of claim 1 wherein R₁ and R₂ are hydrogen, n is 1, X is COH and Z is p-nitrophenylazo.

3. A composition for detecting the presence of lithium ion in solution, said composition comprising the compound of one of claims 1-2, a water miscible organic solvent, and a buffer to adjust the pH of the reagent composition to at least 12.

4. The composition of claim 3 wherein the water miscible organic solvent is diethylene glycol monoethyl ether at a concentration less than 25% volume to volume.

5. The composition of claim 3 further including a surfactant.

6. A method for selectively determining the presence of lithium ions in a test sample comprising the steps of:

(a) contacting said test sample with a reagent composition including a compound which complexes selectivity to the test cation and being the formula:

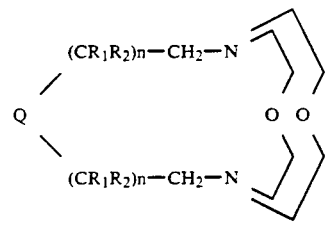

where:

n = 1 or 2,

1 R₁ and R₂, same or different, are hydrogen, lower alkyl, lower alkenyl, or lower alkylidene; and Q is a chromogenic moiety which provides a detectable response upon complexation of said compound with lithium ion and has the structure:

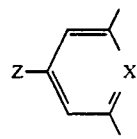

wherein:

X is CH, C-OH or N; and

Z is p-nitrophenylazo, 2,4-dinitrophenylazo, 2,4,6-trinitrophenylazo, p-nitrostyryl, p-benzoquinonemonoimino, bis-(4-dimethylaminophenyl) hydroxymethyl, 3-phenylisothiazolyl-5-azo, thiazolyl-5-azo, or isothiazolyl-5-azo;

(b) measuring the detectable response; and (c) comparing the response so detected with responses measured when said compound is reacted with a series of standard compositions containing known amounts of lithium ions.

7. The method of claim 6 wherein R₁ and R₂ are hydrogen, n is 1, X is COH and Z is p-nitrophenylazo.

8. The method of claim 6 wherein said reagent composition further includes a water miscible solvent and a buffer to maintain the pH of the reagent composition at about at least 12.

9. The method of claim 8 wherein the water miscible organic solvent is diethylene glycol monoethyl ether at a concentration of less than 25% volume to volume.

10. The method of claim 8 wherein the reagent composition further includes a surfactant.

* * * * *